US012670994B2

(12) United States Patent
Godden et al.

(10) Patent No.: US 12,670,994 B2
(45) Date of Patent: Jun. 30, 2026

(54) MACHINE LEARNING TECHNIQUES FOR GENERATING HYBRID RISK SCORES

(71) Applicant: Optum, Inc., Minnetonka, MN (US)

(72) Inventors: Paul J. Godden, London (GB); Gregory J. Boss, Saginaw, MI (US); Daniel George McCreary, St. Louis Park, MN (US); Mark Gregory Megerian, Rochester, MN (US)

(73) Assignee: Optum, Inc., Minnetonka, MN (US)

( * ) Notice: Subject to any disclaimer, the term of this patent is extended or adjusted under 35 U.S.C. 154(b) by 1325 days.

(21) Appl. No.: 17/225,665

(22) Filed: Apr. 8, 2021

(65) Prior Publication Data

US 2022/0122736 A1 Apr. 21, 2022

Related U.S. Application Data

(60) Provisional application No. 63/092,563, filed on Oct. 16, 2020.

(51) Int. Cl.
| | |
|---|---|
| *G16H 50/30* | (2018.01) |
| *G06N 3/045* | (2023.01) |
| *G06N 20/20* | (2019.01) |
| *G16H 50/20* | (2018.01) |

(52) U.S. Cl.
CPC ............. *G16H 50/30* (2018.01); *G06N 3/045* (2023.01); *G06N 20/20* (2019.01); *G16H 50/20* (2018.01)

(58) Field of Classification Search
CPC .......... G06N 3/045; G06N 3/088; G06N 3/12; G06N 3/126; G06N 5/02; G06N 5/045; G06N 3/047; G06N 3/0464; G06N 3/042

USPC .......................................................... 706/21
See application file for complete search history.

(56) References Cited

U.S. PATENT DOCUMENTS

| | | | | |
|---|---|---|---|---|
| 7,006,992 | B1 * | 2/2006 | Packwood ............. | G06Q 40/03 |
| | | | | 705/38 |
| 8,818,932 | B2 * | 8/2014 | Nolan ................... | G06F 40/211 |
| | | | | 706/55 |
| 9,092,391 | B2 | 7/2015 | Stephan et al. | |
| 10,366,335 | B2 | 7/2019 | Schmidt | |
| 10,468,141 | B1 | 11/2019 | Valenzuela et al. | |
| 10,885,464 | B1 | 1/2021 | Bruno et al. | |
| 11,355,246 | B2 * | 6/2022 | Krause ................... | G16H 50/20 |

(Continued)

FOREIGN PATENT DOCUMENTS

| | | |
|---|---|---|
| WO | 2020/077352 A1 | 4/2020 |
| WO | 2020/191195 A1 | 9/2020 |

OTHER PUBLICATIONS

Zitnik et al., Machine Learning for Integrating Data in Biology and Medicine: Principles, Practice, and Opportunities, 2018 (Year: 2018).*

(Continued)

*Primary Examiner* — Hosain T Alam
(74) *Attorney, Agent, or Firm* — Alston & Bird LLP

(57) ABSTRACT

Various embodiments of the present invention provide methods, apparatus, systems, computing devices, computing entities, and/or the like for performing risk score generation predictive data analysis. Certain embodiments of the present invention utilize systems, methods, and computer program products that risk score generation predictive data analysis by utilizing at least one of inferred hybrid risk score generation machine learning models and hybrid graph-based machine learning models.

20 Claims, 8 Drawing Sheets

601

Perform one or more per-embedding genetic programming operations with respect to each graph-based feature embedding to generate a per-embedding genetic programming modeling data object
701

Perform a set of cross-model interactions to generate an overall inferred risk model
702

Evaluate the overall inferred risk model to determine a testing evaluation output
703

Generate the inferred hybrid risk score generation model based on the testing evaluation output
704

(56)                References Cited

U.S. PATENT DOCUMENTS

| 11,556,945 B1 | 1/2023 | Gurumoorthy et al. | |
| 2004/0115701 A1 | 6/2004 | Comings et al. | |
| 2009/0099789 A1 | 4/2009 | Stephan et al. | |
| 2009/0307179 A1 | 12/2009 | Colby et al. | |
| 2010/0042438 A1 | 2/2010 | Moore et al. | |
| 2010/0070455 A1 | 3/2010 | Halperin et al. | |
| 2014/0283085 A1 | 9/2014 | Maestas | |
| 2015/0213449 A1 | 7/2015 | Morrison et al. | |
| 2015/0234999 A1 | 8/2015 | Hu et al. | |
| 2016/0117443 A1 | 4/2016 | Van Ooijen et al. | |
| 2016/0155069 A1* | 6/2016 | Hoover | G06Q 30/06 |
| | | | 706/12 |
| 2016/0226905 A1 | 8/2016 | Baikalov et al. | |
| 2017/0191847 A1 | 7/2017 | Chintakindi et al. | |
| 2017/0206319 A1* | 7/2017 | Attanapola | G16H 50/30 |
| 2017/0281097 A1 | 10/2017 | Thakur et al. | |
| 2017/0357771 A1 | 12/2017 | Connolly et al. | |
| 2018/0192894 A1 | 7/2018 | An et al. | |
| 2018/0246486 A1 | 8/2018 | Krasadakis | |
| 2019/0017119 A1 | 1/2019 | Khera et al. | |
| 2019/0065670 A1 | 2/2019 | Yandell et al. | |
| 2019/0198142 A1 | 6/2019 | Lu et al. | |
| 2019/0216350 A1 | 7/2019 | Sullivan et al. | |
| 2019/0228838 A1 | 7/2019 | Pare et al. | |
| 2020/0005900 A1* | 1/2020 | Cha | G16H 10/40 |
| 2020/0019674 A1 | 1/2020 | Trunck et al. | |
| 2020/0046299 A1 | 2/2020 | An et al. | |
| 2020/0105392 A1 | 4/2020 | Karkazis et al. | |
| 2020/0118647 A1 | 4/2020 | Zhang et al. | |
| 2020/0126671 A1 | 4/2020 | Ziegler et al. | |
| 2020/0167920 A1 | 5/2020 | Hall et al. | |
| 2020/0193327 A1 | 6/2020 | Iwakura et al. | |
| 2020/0227172 A1 | 7/2020 | Perkins et al. | |
| 2020/0251193 A1 | 8/2020 | White et al. | |
| 2020/0342958 A1 | 10/2020 | McGovern et al. | |
| 2021/0065846 A1 | 3/2021 | Rivas et al. | |
| 2021/0089965 A1 | 3/2021 | Bates et al. | |
| 2021/0216928 A1 | 7/2021 | O'Toole et al. | |
| 2021/0240837 A1 | 8/2021 | Tseng et al. | |
| 2021/0249137 A1 | 8/2021 | Dil Nahlieli | |
| 2021/0254164 A1 | 8/2021 | Hamet et al. | |
| 2021/0365306 A1 | 11/2021 | Haldar et al. | |
| 2021/0383927 A1 | 12/2021 | Godden et al. | |
| 2021/0398043 A1 | 12/2021 | Lacey | |
| 2022/0067601 A1 | 3/2022 | Gan et al. | |
| 2022/0070201 A1 | 3/2022 | Almaz et al. | |
| 2022/0100857 A1 | 3/2022 | Filar et al. | |
| 2022/0201141 A1 | 6/2022 | Arakawa | |
| 2022/0327404 A1 | 10/2022 | Godden et al. | |
| 2024/0013064 A1 | 1/2024 | Godden et al. | |

OTHER PUBLICATIONS

Vyas et al., Application of Genetic Programming (GP) Formalism for Building Disease Predictive Models from Protein-Protein Interactions (PPI) Data, 2018 (Year: 2018).*

Luo, Yuan, Towards Unified Biomedical Modeling with Subgraph Mining and Factorization Algorithms, 2015 (Year: 2015).*

"Coverage (Genetics)," Wikipedia, (3 pages), (online), [Retrieved from the Internet Oct. 21, 2021] <URL: https://en.wikipedia.org/wiki/Coverage_(genetics)>.

"Factor V Leiden," Mayo Clinic, (5 pages), (online), [Retrieved from the Internet Oct. 21, 2021] <https://u-prevent.com/>.

"Highlights of Prescribing Information—Keytruda," (93 pages), (online), [Retrieved from the Internet Oct. 21, 2021] <URL: https://www.accessdata.fda.gov/drugsatfda_docs/label/2020/125514s084lbl.pdf>.

Myriad Announces New Studies Validating the Ability of Myriad's riskScore Test to Modify Breast Cancer Risk Prediction, GlobeNewswire, Jul. 7, 2020, (4 pages), available online: https://www.globenewswire.com/en/news-release/2020/07/07/2058466/15459/en/Myriad-Announces-New-Studies-Validating-the-Ability-of-Myriad-s-riskScore-Test-to-Modify-Breast-Cancer-Risk-Prediction.html.

"NCCN Clinical Practice Guidelines in Oncology (NCCN Guidelines) with NCCN Evidence Blocks," National Comprehensive Cancer Network, (3 pages), (online), [Retrieved from the Internet Oct. 21, 2021] <URL: https://www.nccn.org/guidelines/guidelines-with-evidence-blocks>.

"Test ID: T790M Cell-Free DNA EGFR T790M Mutation Analysis, Blood," Mayo Clinic Laboratories, pp. 1-4, (article, online), [Retrieved from the Internet Oct. 21, 2021] <URL: https://www.mayocliniclabs.com/test-catalog/download-setup.php?format=pdf&unit_code=113410>.

"U-Prevent: You Are in Control," (online), (3 pages), [Retrieved from the Internet Oct. 21, 2021] <URL: https://u-prevent.com/>.

Alvarez, Jean G. Bustamante et al. "Agents to Treat BRAF-Mutant Lung Cancer," Drugs in Context, vol. 8, No. 212566, pp. 1-5, Mar. 13, 2019, DOI: 10.7573/dic.212566, PMCID: PMC6419923, PMID: 30899313.

Dewey, Frederick E. et al. "Clinical Interpretation and Implications of Whole-Genome Sequencing," The Journal of the American Medical Association (JAMA), Mar. 12, 2014, vol. 311, No. 10, pp. 1035-1045, DOI: 10.1001/jama.2014.1717, PMCID: PMC4119063, NIHMSID: NIHMS585722, PMID: 24618965.

Mechanic, Leah E et al. "Common Genetic Variation in TP53 Is Associated With Lung Cancer Risk and Prognosis in African Americans and Somatic Mutations in Lung Tumors," Cancer Epidemiology, Biomarkers & Prevention, vol. 16, No. 2, Feb. 2007, pp. 214-222, DOI: 10.1158/1055-9965.EPI-06-0790.

Suda, Kenichi et al. "EGFR T790M Mutation: A Double Role in Lung Cancer Cell Survival," Journal of Thoracic Oncology, vol. 4, No. 1, Jan. 2009, pp. 1-4, DOI: 10.1097/JTO.0b013e3181913c9f.

Wells, Alex et al. "Ranking of Non-Coding Pathogenic Variants and Putative Essential Regions of the Human Genome," Nature Communications, vol. 10, No. 5241, Nov. 20, 2019, pp. 1-9, DOI: 10.1038/s41467-019-13212-3.

Patents Court, "Protecting Kids the World Over (PKTWO) Ltd's Patent Application," Reports of Patent, Design and Trade Mark Cases, vol. 129, Issue 5, May 2012, pp. 323-335, available online <https://doi.org/10.1093/rpc/rcs022>.

Non-Final Rejection Mailed on Sep. 20, 2024 for U.S. Appl. No. 17/382,691, 40 page(s).

"ClinicalTrials.gov," U.S. National Library of Medicine, [Retrieved from the Internet Nov. 8, 2022] <URL: https://clinicaltrials.gov/ct2/home>.

"DMD Gene-Gene Cards|DMD Protein|DMD Antibody," GeneCards—The Human Gene Database, (28 pages), [Retrieved from the Internet Aug. 22, 2022] <URL: https://www.genecards.org/cgi-bin/carddisp.pl?gene=DMD&keywords=dystrophin>.

"Genetic Testing Clinical Trials," Mayo Clinic Research, (7 pages), [Retrieved from the Internet Aug. 11, 2022] <URL: https://www.mayo.edu/research/clinical-trials/tests-procedures/genetic-testing>.

"Population Genetics—Homo Sapiens," el Ensembl Genome Browser 107, (5 pages), [Retrieved from the Internet Aug. 11, 2022] <URL: http://useast.ensembl.org/Homo_sapiens/Variation/Population?db=core;r=6:73415665-73416665;v=rs311685;vdb=variation;vf=167346058>.

"Search of: Genetic Testing|Recruiting Studies—List of Results," ClinicalTrials.gov, NIH: U.S. National Library of Medicine, (5 pages), [Retrieved from the Internet Aug. 11, 2022] <URL: https://clinicaltrials.gov/ct2/results?term=genetic+testing&Search=Apply&recrs=a&age_v=&gndr=&type=&rslt=>.

"The International Parkinson Disease Genomics Consortium (IPDGC)," (3 pages), [Retrieved from the Internet Aug. 11, 2022] <URL: https://pdgenetics.org/>.

De Boer, N. et al. "Longitudinal Associations Between Alcohol Use, Smoking, Genetic Risk Scoring and Symptoms of Depression in the General Population: A Prospective 6-Year Cohort Study," Psychological Medicine, pp. 1-9, Jul. 5, 2021, DOI: 10.1017/S0033291721002968.

Frank, Phillip et al. "Genetic Susceptibility, Inflammation and Specific Types of Depressive Symptoms: Evidence From the Eng-

(56) References Cited

OTHER PUBLICATIONS lish Longitudinal Study of Ageing," Translational Psychiatry, vol. 10, No. 140, pp. 1-9, May 12, 2020, DOI: 10.1038/s41398-020-0815-9.

Hebbar, Prashantha et al. "Genome-Wide Association Study Identifies Novel Risk Variants From RPS6KA1, CADPS, VARS, and DHX58 for Fasting Plasma Glucose in Arab Population," Scientific Reports, vol. 10, No. 152, (17 pages), Jan. 13, 2020, DOI: 10.1038/s41598-019-57072-9.

Joffe, Erel et al. "Clinical Trials in the Genomic Era," Journal of Clinical Oncology, vol. 35, No. 9, Mar. 20, 20217, pp. 1011-1017.

Leonard, Hampton et al. "Genetic Variability and Potential Effects on Clinical Trial Outcomes: Perspectives in Parkinson's Disease," Journal of Medical Genetics, vol. 57, Issue 5, pp. 331-338, Oct. 2, 2019 (ePub: Nov. 29, 2019), doi: 10.1136/jmedgenet-2019-106283.

Nayak, Barun Kumar. "Understanding the Relevance of Sample Size Calculation," Indian Journal of Ophthalmology, vol. 58, No. 6, pp. 469-470, Nov.-Dec. 2010, DOI: 10.4103/0301-4738.71673.

Phillips, Kathryn A. et al. "Genetic Test Availability And Spending: Where Are We Now? Where Are We Going?," Health Affairs, vol. 37, No. 5, pp. 710-716, May 2018, DOI: 10.1377/hlthaff.2017.1427.

Qiu, Fang et al. "A Genome-Wide Association Study Identifies Six Novel Risk Loci for Primary Biliary Cholangitis," Nature Communications, vol. 8, No. 14828, pp. 1-8, Apr. 20, 2017, DOI: 10.1038/ncomms14828.

Sadler, Georgia Robins et al. "Costs of Recruiting Couples to a Clinical Trial," Contemporary Clinical Trials, vol. 28, Issue 4, pp. 423-432, Jul. 2007, (Author Manuscript: PubMed Central, Feb. 10, 2010), DOI: 10.1016/j.cct.2006.11.006.

Sultana, Janet et al. "Clinical and Economic Burden of Adverse Drug Reactions," Journal of Pharmacology & Pharmacotherapeutics, vol. 4 (Supplement 1), pp. S73-S77, Dec. 4, 2013, DOI: 10.4103/0976-500X.120957.

Trzupek, Karmen et al. "Adding Genetics to the Clinical Trial Ecosystem," MedCity News, Dec. 2018, (8 pages), (article), [Retrieved from the Internet Aug. 11, 2022] <URL: https://medcitynews.com/2018/12/adding-genetics-to-the-clinical-trial-ecosystem/>.

Yeboah, Joseph et al. "Comparison of Novel Risk Markers for Improvement in Cardiovascular Risk Assessment in Intermediate-Risk Individuals," Journal of American Medical Association (JAMA), vol. 308, No. 8, pp. 788-795, Aug. 22-29, 2012, DOI: 10.1001/jama.2012.9624.

"Incremental Learning," Wikipedia, (2 pages), (article, online), [Retrieved from the Internet Jul. 8, 2021] <https://en.wikipedia.org/wiki/Incremental_learning>.

"Non-Small Cell Lung Cancer—*Homo Sapiens* (Human)," KEGG Pathway, Sep. 4, 2020, (1 page), (article online), [Retrieved from the Internet Jul. 8, 2021} <https://www.genome.jp/kegg-bin/show_pathway?hsa05223>.

"Sequence Read Archive (SRA)—Now Available on the Cloud," (article, online), (1 page), [Retrieved from the Internet Jul. 8, 2021] <https://www.ncbi.nlm.nih.gov/sra>.

Alaa, Ahmed M. et al. "Demystifying Black-Box Models With Symbolic Metamodels," 33rd Conference on Advances in Neural Information Processing Systems, (NeurIPS 2019), (11 pages), Vancouver, Canada, [available online] <https://proceedings.neurips.cc/paper/2019/file/567b8f5f423af15818a068235807edc0-Paper.pdf>.

Bonnett, Laura J. et al. "Guide to Presenting Clinical Prediction Models for Use in Clinical Settings," The BMJ, vol. 365, No. 1737, Feb. 8, 2019, pp. 1-8, DOI: 10.1136/bmj.1737.

Cranmer, Miles et al. "Discovering Symbolic Models From Deep Learning With Inductive Biases" arXiv:2006.11287v2 [cs.LG] Nov. 18, 2020, (25 pages), [available online] <https://arxiv.org/pdf/2006.11287.pdf>.

Gibson, Greg. "On the Utilization of Polygenic Risk Scores for Therapeutic Targeting," PLoS Genetics, vol. 15, No. 4:e1008060, Apr. 25, 2019, pp. 1-14, DOI: 10.1371/journal.pgen.1008060.

Grover, Aditya et al. "node2vec: Scalable Feature Learning for Networks," arXiv:1607.00653v1 [cs.SI] Jul. 3, 2016, (10 pages).

Ho, Daniel Sik Wai et al. "Machine Learning SNP Based Prediction for Precision Medicine," Frontiers in Genetics, vol. 10, Article 267, Mar. 27, 2019, (pp. 1-10), DOI: org/10.3389/fgene.2019.00267.

Luo, Yuan et al. "ScanMap: Supervised Confounding Aware Non-Negative Matrix Factorization for Polygenic Risk Modeling," Proceedings of Machine Learning Research,, vol. 126, Sep. 18, 2020, pp. 1-18.

Ritchie, Marylyn D. et al. "Genetic Programming Neural Networks: A Powerful Bioinformatics Tool for Human Genetics," NIH Public Access, Author Manuscript, Applied Soft Computing, vol. 7, No. 1, Jan. 2007, (25 pages), DOI: 10.1016/j.asoc.2006.01.013.

Schmidt, Michael et al. "Symbolic Regression of Implicit Equations," Genetic Programming Theory and Practice VII, Genetic and Evolutionary Computation, Oct. 20, 2009, pp. 73-85, DOI: 10.1007/978-1-4419-1626-6_5.

Siddiqui, Mohammad R. et al. "Targeting Epidermal Growth Factor Receptor (EGFR) and Human Epidermal Growth Factor Receptor 2 (HER2) Expressing Bladder Cancer Using Combination Photoimmunotherapy (PIT)," Scientific Reports, vol. 9, No. 2084, Feb. 14, 2019, pp. 1-14, DOI: 10.1038/s41598-019-38575-x.

Final Rejection Mailed on Feb. 25, 2025 for U.S. Appl. No. 17/382,691, 43 page(s).

Brownlee, J. et al. "Ensemble Learning Methods for Deep Learning Neural Networks." Available at https://www.machinelearningmastery.com/ensemble-methods-for-deep-learning-neural-networks/ (Year: 2019).

Mundhenk, T. et al. "Symbolic Regression via Neural-Guided Genetic Programming Population Seeding." Available at https://arxiv.org/pdf/2111.00053 (Year: 2021).

Nakamura, K. et al. "Health improvement framework for planning actionable treatment process using surrogate Bayesian model." Available at https://arxiv.org/pdf/2010.16087 (Year: 2020).

Non-Final Rejection Mailed on Jul. 10, 2025 for U.S. Appl. No. 17/811,229, 105 page(s).

Zhang, Q. et al. "DSpin: Detecting Automatically Spun Content on the Web." Available at https://cseweb.ucsd.edu/~voelker/pubs/dspin-ndss14.pdf (Year: 2014).

Non-Final Rejection Mailed on Oct. 1, 2025 for U.S. Appl. No. 17/382,691, 61 page(s).

Final Rejection Mailed on Feb. 13, 2026 for U.S. Appl. No. 17/811,229, 45 page(s).

Final Rejection Mailed on Feb. 18, 2026 for U.S. Appl. No. 17/382,691, 25 page(s).

Punitha, V., et al., "Traffic classification for efficient load balancing in server cluster using deep learning technique," The Journal of Supercomputing, published online Jan. 12, 2021, vol. 77, retrieved from the Internet at https://search.ebscohost.com/login.aspx?direct=true&profile=ehost&scope=site&authtype=crawler&jrnl=09208542&AN=151441969&h, pp. 8038-8062.

* cited by examiner

Client Computing Entities 102

Predictive Data Analysis Computing Entity 106

Storage Subsystem 108

Predictive Data Analysis System 101

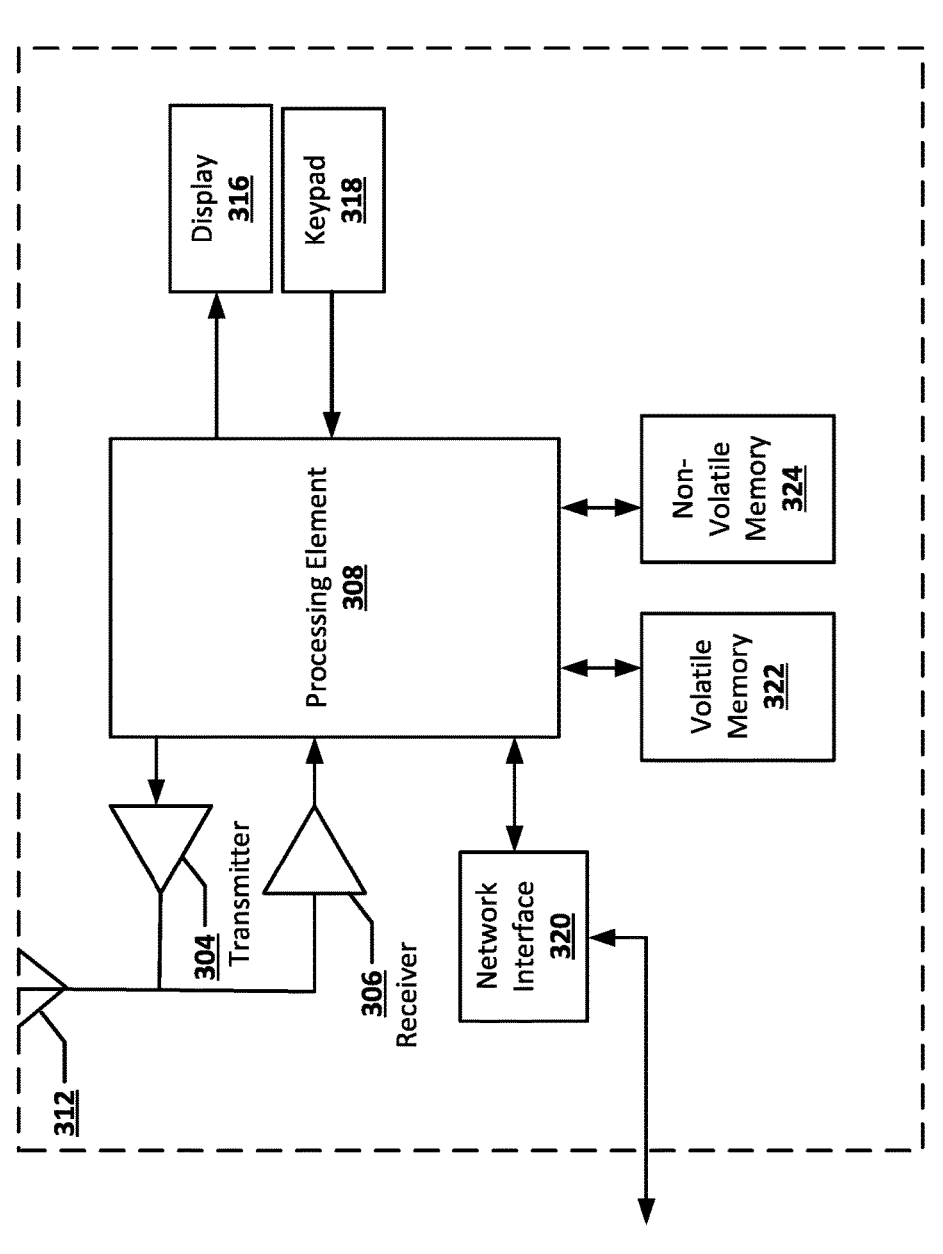
FIG. 3

Identify a trained hybrid graph-based machine learning model
401

Generate an inferred hybrid risk score generation machine learning model using the trained hybrid graph-based machine learning model
402

401

Perform a set of explanatory data analysis operations to
generate a set of ground-truth risk tensors for each ground-truth
patient data object
501

Generate a set of refined ground-truth risk tensors for each
ground-truth patient data object
502

Generate a set of ground-truth feature embeddings for each
ground-truth patient data object
503

Generate a trained hybrid graph-based machine learning model
504

FIG. 5

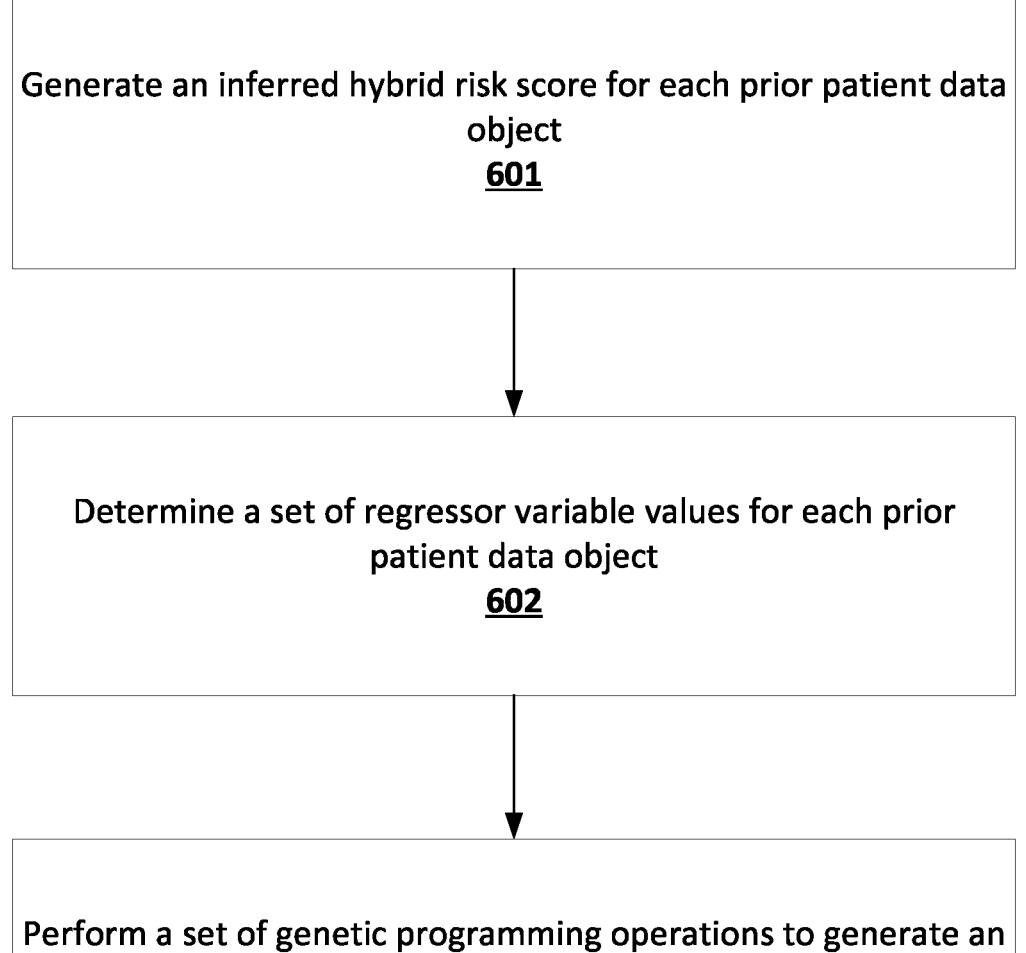
FIG. 6

601

Perform one or more per-embedding genetic programming
operations with respect to each graph-based feature embedding
to generate a per-embedding genetic programming modeling
data object
701

Perform a set of cross-model interactions to generate an overall
inferred risk model
702

Evaluate the overall inferred risk model to determine a testing
evaluation output
703

Generate the inferred hybrid risk score generation model based
on the testing evaluation output
704

FIG. 7

MACHINE LEARNING TECHNIQUES FOR GENERATING HYBRID RISK SCORES

CROSS-REFERENCES TO RELATED APPLICATION(S)

The present application claims priority to U.S. Provisional Patent Application No. 63/092,563 (filed Oct. 16, 2020), which is incorporated herein by reference in its entirety.

BACKGROUND

Various embodiments of the present invention address technical challenges related to performing predictive data analysis and provide solutions to address the efficiency and reliability shortcomings of existing predictive data analysis solutions.

BRIEF SUMMARY

In general, various embodiments of the present invention provide methods, apparatus, systems, computing devices, computing entities, and/or the like for performing risk score generation predictive data analysis. Certain embodiments of the present invention utilize systems, methods, and computer program products that perform risk score generation predictive data analysis by utilizing at least one of inferred hybrid risk score generation machine learning models and hybrid graph-based machine learning models.

In accordance with one aspect, a method is provided. In one embodiment, the method comprises: processing a plurality of graph feature embedding data objects for a patient data object using an inferred hybrid risk score generation machine learning model to generate a hybrid risk score, wherein: (i) the inferred hybrid risk score generation machine learning model is generated using a set of genetic programming operations, (ii) the set of genetic programming operations are performed based at least in part on a set of inferred hybrid risk scores for a set of prior patient data objects, and (iii) each inferred hybrid risk score of the set of inferred hybrid risk scores is generated by processing a plurality of prior graph feature embedding data objects for a corresponding prior patient data object of the set of patient data objects using a hybrid graph-based machine learning model; and performing one or more prediction-based actions based at least in part on the hybrid risk score.

In accordance with another aspect, a computer program product is provided. The computer program product may comprise at least one computer-readable storage medium having computer-readable program code portions stored therein, the computer-readable program code portions comprising executable portions configured to: process a plurality of graph feature embedding data objects for a patient data object using an inferred hybrid risk score generation machine learning model to generate a hybrid risk score, wherein: (i) the inferred hybrid risk score generation machine learning model is generated using a set of genetic programming operations, (ii) the set of genetic programming operations are performed based at least in part on a set of inferred hybrid risk scores for a set of prior patient data objects, and (iii) each inferred hybrid risk score of the set of inferred hybrid risk scores is generated by processing a plurality of prior graph feature embedding data objects for a corresponding prior patient data object of the set of patient data objects using a hybrid graph-based machine learning model; and perform one or more prediction-based actions based at least in part on the hybrid risk score.

In accordance with yet another aspect, an apparatus comprising at least one processor and at least one memory including computer program code is provided. In one embodiment, the at least one memory and the computer program code may be configured to, with the processor, cause the apparatus to: process a plurality of graph feature embedding data objects for a patient data object using an inferred hybrid risk score generation machine learning model to generate a hybrid risk score, wherein: (i) the inferred hybrid risk score generation machine learning model is generated using a set of genetic programming operations, (ii) the set of genetic programming operations are performed based at least in part on a set of inferred hybrid risk scores for a set of prior patient data objects, and (iii) each inferred hybrid risk score of the set of inferred hybrid risk scores is generated by processing a plurality of prior graph feature embedding data objects for a corresponding prior patient data object of the set of patient data objects using a hybrid graph-based machine learning model; and perform one or more prediction-based actions based at least in part on the hybrid risk score.

BRIEF DESCRIPTION OF THE DRAWINGS

Figure 1:

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
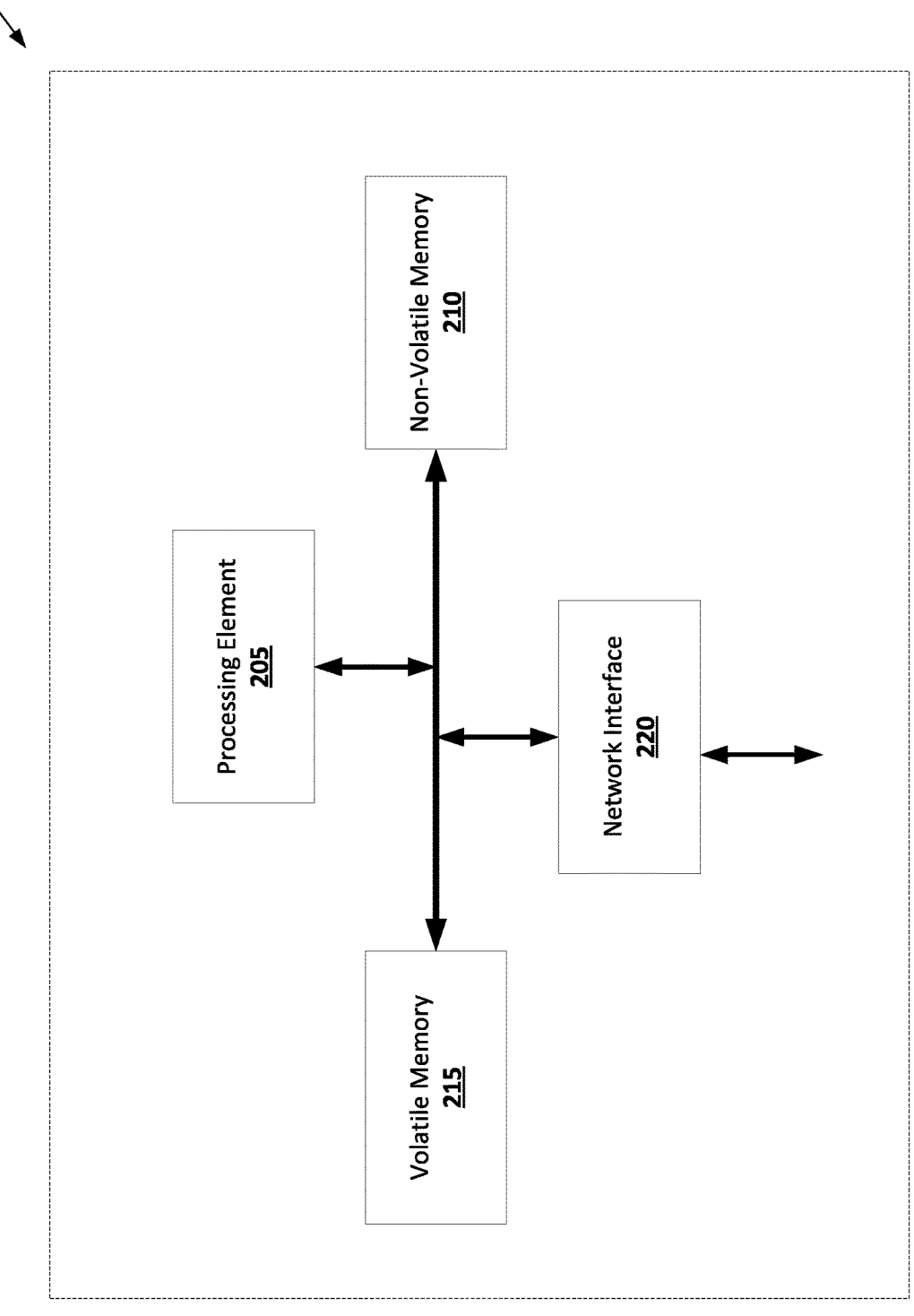

FIG. 2 provides an example predictive data analysis computing entity in accordance with some embodiments discussed herein.

FIG. 3 provides an example client computing entity in accordance with some embodiments discussed herein.

Figure 4:

FIG. 4 is a flowchart diagram of an example process for generating an inferred hybrid risk score generation machine learning model in accordance with some embodiments discussed herein.

FIG. 5 is a flowchart diagram of an example process for generating a trained hybrid graph-based machine learning model in accordance with some embodiments discussed herein.

FIG. 6 is a flowchart diagram of an example process for generating an inferred hybrid risk score generation machine learning model using a trained hybrid graph-based machine learning model in accordance with some embodiments discussed herein.

FIG. 7 is a flowchart diagram of an example process for generating an inferred hybrid risk score generation machine learning model using a trained hybrid graph-based machine learning model in accordance with some embodiments discussed herein.

Figure 8:
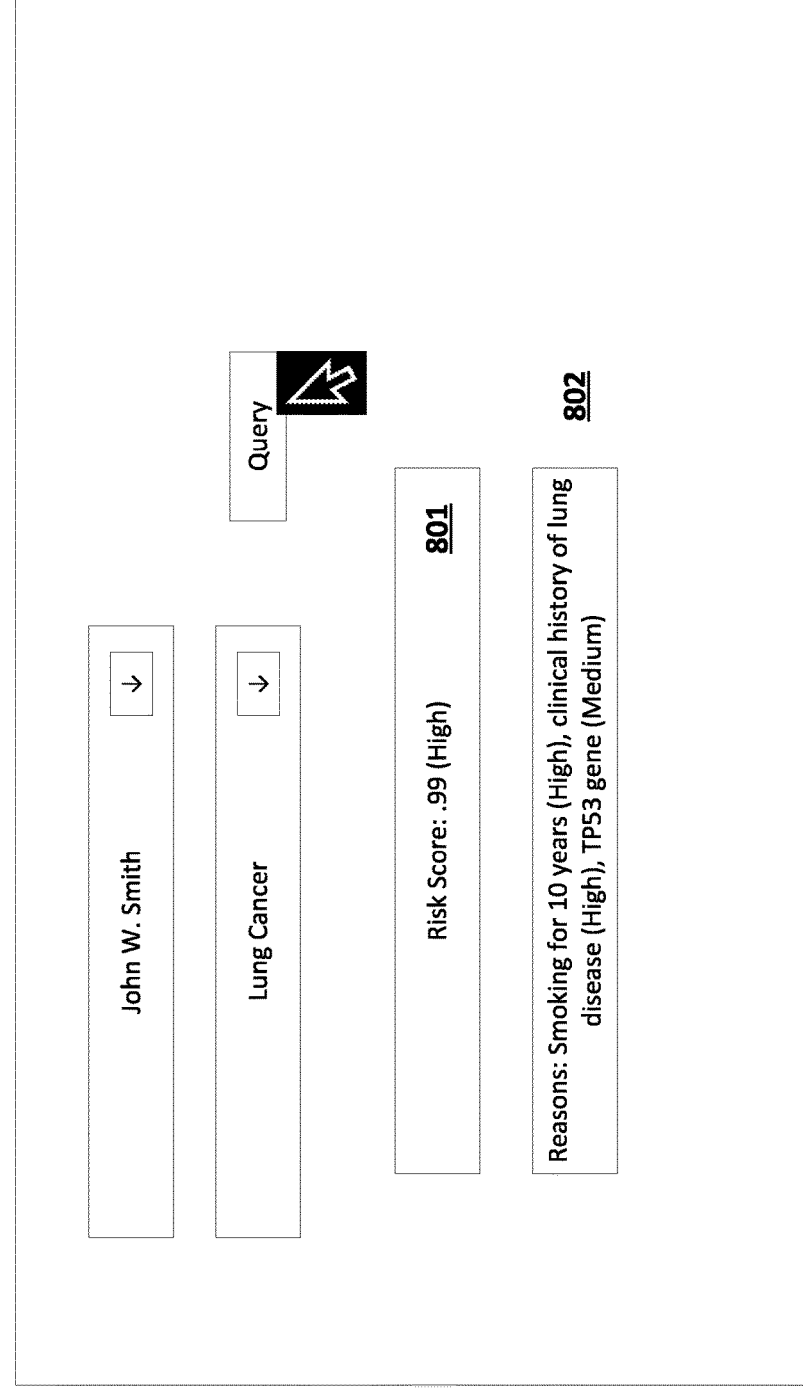

FIG. 8 provides an operational example of a prediction output user interface in accordance with some embodiments discussed herein.

DETAILED DESCRIPTION

Various embodiments of the present invention now will be described more fully hereinafter with reference to the accompanying drawings, in which some, but not all, embodiments of the inventions are shown. Indeed, these inventions may be embodied in many different forms and should not be construed as limited to the embodiments set forth herein; rather, these embodiments are provided so that this disclosure will satisfy applicable legal requirements.

The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. Overview and Technical Improvements

Various embodiments of the present invention improve the computational efficiency of performing risk score generation predictive data analysis by describing reliable inferred hybrid risk score generation machine learning models that are trained based at least in part on performing genetic programming operations on the inferred outputs generated by another machine learning model, such as the inferred outputs generated by a hybrid graph-based machine learning model. The inferred hybrid risk score generation machine learning models described and enabled by various embodiments of the present invention often require relatively little computationally resources (including processing resources and memory resources) to execute. This is because genetic programming operations (e.g., symbolic regression operations) are able to infer often non-complex algebraic relationships between inputs to the inferred hybrid risk score generation machine learning models, a feature that both reduces the runtime cost of performing predictive inferences using the noted inferred hybrid risk score generation machine learning models and improves the need for storing complex configuration data for the inferred hybrid risk score generation machine learning models in order to enable performing predictive inferences using the inferred hybrid risk score generation machine learning models. In this way, various embodiments of the present invention improve both computational efficiency and storage-wise efficiency of performing risk score generation predictive data analysis and make important technical contributions to the field of predictive data analysis in relation to machine learning techniques for generating risk scores. While various embodiments of the present invention discuss performing a set of genetic programming operations, a person of ordinary skill in the relevant technology will recognize that operations to any evolutionary optimization computational method may be used.

Moreover, various embodiments of the present invention improve interpretability of performing risk score generation machine learning models. The inferred hybrid risk score generation machine learning models described and enabled by various embodiments of the present invention describe interpretable relationships between regressor variables, a feature that in turn enables a predictive data analysis system to generate explanatory metadata for a generated hybrid risk score. In this way, various embodiments of the present invention improve interpretability of performing risk score generation predictive data analysis and make important technical contributions to the field of predictive data analysis in relation to machine learning techniques for generating risk scores.

II. Definitions

The term "trained hybrid graph-based machine learning model" may refer to a data entity that is configured to describe parameters, hyper-parameters, and/or defined operations of a trained machine learning model that is configured to process one or more graph-based feature embeddings for a patient data object in order to generate an inferred hybrid risk score for the patient data object. The trained hybrid graph-based machine learning model may be configured to receive, as at least a part of its inputs, one or more graph-based feature embeddings for a patient data object, where a graph-based feature embedding may be a vector of one or more values that are determined based at least in part on a risk tensor of one or more risk tensors for the patient data object. In some embodiments, the trained hybrid graph-based machine learning model may include: a plurality of graph-based machine learning models (e.g., including one or more graph convolutional neural network machine learning models), where each graph-based machine learning model is configured to process a graph-based feature embedding having a particular graph-based feature embedding type to generate a per-model machine learning output, and an ensemble machine learning model that is configured to aggregate/combine per-model machine learning outputs across various graph-based machine learning models to generate the inferred hybrid risk score for the patient data object. For example, a trained hybrid graph-based machine learning model may include: a first graph-based machine learning model that is configured to process a graph-based feature embedding determined based at least in part on genomic data (e.g., based at least in part on a genomic risk tensor) for a patient data object in order to generate a first per-model machine learning output, a second graph-based machine learning model that is configured to process a graph-based feature embedding determined based at least in part on clinical data (e.g., based at least in part on a clinical risk tensor) for a patient data object in order to generate a second per-model machine learning output, a third graph-based machine learning model that is configured to process a graph-based feature embedding determined based at least in part on behavioral data (e.g., based at least in part on a behavioral risk tensor) for a patient data object in order to generate a third per-model machine learning output, and an ensemble machine learning model that is configured to aggregate/combine the first per-model machine learning output, the second per-model machine learning output, and the third per-model machine learning output in order to generate the inferred hybrid risk score for the patient data object. In some embodiments, the trained hybrid graph-based machine learning model is trained (e.g., via one or more end-to-end training operations) using ground-truth hybrid risk scores for a set of ground-truth graph-based feature embeddings for each training patient data object of a set of training patient data objects.

The term "risk tensor" may refer to a data entity that is configured to describe a tensor data object that describes a set of subject-matter-defined data items associated with a patient data object. In some embodiments, a risk tensor describes a heterogeneous group of data that are related by the underlying risk tensor. Examples of risk tensors include a genomic risk tensor that includes genomic data associated with a patient data object, a behavioral risk tensor that includes behavioral data associated with a patient data object, a clinical risk tensor that includes clinical data associated with a patient data object, a demographic risk tensor that includes demographic data associated with a patient data object, a health history risk tensor that includes health history data associated with a patient data object, and/or the like. For example, a genomic risk tensor may describe at least one of ribonucleic acid (RNA)-seq data, complex molecular biomarkers relating to oncology (e.g.

tumor mutational burden), single nucleotide polymorphisms, deoxyribonucleic acid (DNA) methylation data from panels, and/or the like. In some embodiments, all of the noted data items may be grouped, because they are all related to the genomic risk profile for a given disease, even though the data items are different, relate to different aspects of the genome, and come in different file formats (e.g. FASTQ files for DNA data, .IDAT files for Illumina Infinium HumanMethylation450 chip data, and/or the like). In some embodiments, if specific data items are assumed, from existing clinical practice, to be highly influential (e.g. smoking status and pack history for lung cancer), then a confidence score in the relevance of each risk tensor, and the necessary volumes of data, may be generated. The output from the confidence score can be used to assess whether there are sufficient data to adopt the risk tensor data, or whether additional data are recommended (e.g. data augmentation is needed in the case of medical image data). In some embodiments, when a risk tensor is used to generate a trained hybrid graph-based machine learning model (e.g., by generating ground-truth graph-based feature embeddings that are used as inputs during the training of a hybrid graph-based machine learning model), the risk tensor is referred to as a ground-truth risk tensor. In some embodiments, when a risk tensor is used to generate inferred hybrid risk scores that are in turn used to generate an inferred hybrid risk score generation machine learning model, the risk tensor is referred to as a prior risk tensor.

The term "graph-based feature embedding" may refer to a data entity that is configured to describe a graph-based representation of a risk tensor. In some embodiments, to generate a graph-based representation of a risk tensor, a predictive data analysis computing entity may embed/convert/transform data items in the given risk tensor into a graph (e.g., a multiplex graph) representation (e.g., by converting the risk tensor into a graph embedding, for example by using a Node2Vec feature embedding routine). For example, given a genomic risk tensor, if suitable genomic networks for any diseases under consideration are available from the Kyoto Encyclopedia of Genes and Genomes (KEGG) resource (e.g. for non-small cell lung cancer the genomic pathway, available online at https://www.genome.jp/kegg-bin/show_pathway?hsa05223), then the pathway may be converted to a graph representation in order to generate a graph-based feature embedding for the genomic risk tensor. In some embodiments, when a graph-based feature embedding is used to generate a trained hybrid graph-based machine learning model (e.g., by using ground ground-truth graph-based feature embeddings as inputs during the training of a hybrid graph-based machine learning model), the graph-based feature embedding is referred to as a ground-truth graph-based feature embedding. In some embodiments, when a graph-based feature embedding is used to generate inferred hybrid risk scores that are in turn used to generate an inferred hybrid risk score generation machine learning model, the graph-based feature embedding is referred to as a prior graph-based feature embedding.

The term "inferred hybrid risk score generation machine learning model" may refer to a data entity that is configured to describe parameters, hyper-parameters, and/or defined operations of a model that relates one or more graph-based feature embeddings for a patient data object to an inferred hybrid risk score generation machine learning model. For example, the inferred hybrid risk score generation machine learning model may be determined by performing one or more genetic programming operations (e.g., including one or more symbolic regression operations) based at least in part on sets of prior graph-based feature embeddings for a set of prior patient data objects and a set of corresponding inferred hybrid risk scores for the set of prior patient data objects, where an inferred hybrid risk score for a prior patient data object may be determined by processing the set of prior graph-based feature embeddings for the prior patient data object using a trained hybrid graph-based machine learning model, and where the set of prior graph-based feature embeddings for a prior patient data object may be supplied as input variables and/or as regressor variables for the one or more genetic programming operations performed to generate the inferred hybrid risk score generation machine learning model. The inferred hybrid risk score generation machine learning model may be configured to process, as inputs, a set of graph-based feature embeddings and generate, as an output, an inferred hybrid risk score, where each graph-based feature embedding may be a vector, and where each inferred hybrid risk score may be an atomic value or a vector.

The term "inferred hybrid risk score" may refer to a data entity that is configured to describe a risk score that is generated by a trained hybrid graph-based machine learning model by processing a set of graph-based feature embeddings for a corresponding patient data object. For example, the inferred hybrid risk score for a particular patient data object (e.g., corresponding to a patient) may be generated by processing (using a trained hybrid graph-based machine learning model) the genomic graph-based feature embedding for the particular patient data object as determined based at least in part on the genomic risk tensor for the particular patient data object, the clinical graph-based feature embedding for the particular patient data object as determined based at least in part on the clinical risk tensor for the particular patient data object, and the behavioral graph-based feature embedding for the particular patient data object based at least in part on the behavioral risk tensor for the particular patient data object. The inferred hybrid risk score may be a vector. An inferred hybrid risk score may be an input variable of an inferred hybrid risk score generation machine learning model. In some embodiments, a predictive data analysis computing entity determines a set of regressor variables for each prior patient data object of a set of prior patient data objects based at least in part on the set of prior graph-based feature embeddings for the prior patient data object. In some embodiments, using the initial candidate equations for the per-model machine learning output associated with each individual graph-based feature embeddings, the predictive data analysis computing entity determines the regressor variables. In some embodiments, the regressor variables are determined based at least in part on techniques for determining separate and interpretable internal functions as described in Crammer et al., "Discovering Symbolic Models from Deep Learning with Inductive Biases" (2020), arXiv:2006.11287v2, available online at https://arxiv.org/pdf/2006.11287.pdf. In some embodiments, a priori, a predictive data analysis computing entity over-estimates the number of regressor variables so that the algorithm can reduce the parameter space (start broad and wide, narrow down via symbolic regression to the smallest equations that match the positive class for risk) of the inferred hybrid risk score generation machine learning model. In some embodiments, the predictive data analysis computing entity bootstraps a candidate risk equation, such as a standard polygenic risk score (PRS) model, to accelerate generating inferred risk scores.

The term "per-embedding genetic programming modeling data object" may refer to a data entity that is configured to describe a model that relates a corresponding prior graph-based feature embedding for a patient data object to an inferred hybrid risk score for the patient data object. In some embodiments, a predictive data analysis computing entity performs one or more per-embedding genetic programming operations with respect to each prior graph-based feature embedding for the prior patient data object to generate a per-embedding genetic programming modeling data object for the prior graph-based feature embedding. In some embodiments, a predictive data analysis computing entity performs a set of cross-model interactions across each per-embedding genetic programming modeling data object for a prior graph-based feature embedding to generate an overall inferred risk model for the model generation epoch. In some embodiments, at each model generation epoch, the predictive data analysis computing entity performs cross-tensor interaction across the per-embedding genetic programming modeling data objects to generate an overall inferred risk model. Such cross-learning interactions may occur, for example, per each training epoch.

III. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations. Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Architecture

FIG. 1 is a schematic diagram of an example architecture 100 for performing predictive data analysis. The architecture 100 includes a predictive data analysis system 101 configured to receive predictive data analysis requests from client computing entities 102, process the predictive data analysis requests to generate predictions, provide the generated predictions to the client computing entities 102, and automatically perform prediction-based actions based at least in part on the generated predictions. An example of a prediction-based action that can be performed using the predictive data analysis system 101 is a request for generating a disease risk score based at least in part on at least one of patient genomic data, patient behavioral data, patient clinical data, and/or the like.

In some embodiments, predictive data analysis system 101 may communicate with at least one of the client computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive data analysis system 101 may include a predictive data analysis computing entity 106 and a storage subsystem 108. The predictive data analysis computing entity 106 may be configured to receive predictive data analysis requests from one or more client computing entities 102, process the predictive data analysis requests to generate predictions corresponding to the predictive data analysis requests, provide the generated predictions to the client computing entities 102, and automatically perform prediction-based actions based at least in part on the generated predictions.

The storage subsystem 108 may be configured to store input data used by the predictive data analysis computing entity 106 to perform predictive data analysis as well as model definition data used by the predictive data analysis computing entity 106 to perform various predictive data analysis tasks. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include, or be in communication with, one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include, or be in communication with, non-volatile media (also referred to as non-volatile storage, memory, memory storage, memory circuitry and/or similar terms used herein interchangeably). In one embodiment, the non-volatile storage or memory may include one or more non-volatile storage or memory media 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the predictive data analysis computing entity 106 may further include, or be in communication with, volatile media (also referred to as volatile storage, memory, memory storage, memory circuitry and/or similar terms used herein interchangeably). In one embodiment, the volatile storage or memory may also include one or more volatile storage or memory media 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1X (1xRTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include, or be in communication with, one or more input elements, such as a keyboard input, a mouse input, a touch screen/display input, motion input, movement input, audio input, pointing device input, joystick input, keypad input, and/or the like. The predictive data analysis computing entity 106 may also include, or be in communication with, one or more output elements (not shown), such as audio output, video output, screen/display output, motion output, movement output, and/or the like.

Exemplary Client Computing Entity

FIG. 3 provides an illustrative schematic representative of an client computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 can be operated by various parties. As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the predictive data analysis computing entity 106. In a particular embodiment, the client computing entity 102 may operate in accordance with multiple wireless communication standards and protocols, such as UMTS, CDMA2000, 1xRTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the predictive data analysis computing entity 106 via a network interface 320.

Via these communication standards and protocols, the client computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to one embodiment, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the client computing entity's 102 position in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the predictive data analysis computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the client computing entity 102. As indicated, this may include a user application that is resident on the entity or accessible through a browser or other user interface for communicating with the predictive data analysis computing entity 106 and/or various other computing entities.

In another embodiment, the client computing entity 102 may include one or more components or functionality that are the same or similar to those of the predictive data analysis computing entity 106, as described in greater detail above. As will be recognized, these architectures and descriptions are provided for exemplary purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. Exemplary System Operations

As discussed in greater detail below, various embodiments of the present invention improve the computational efficiency of performing risk score generation predictive data analysis by describing reliable inferred hybrid risk score generation machine learning models that are trained based at least in part on performing genetic programming operations on the inferred outputs generated by another machine learning model, such as the inferred outputs generated by a hybrid graph-based machine learning model. The inferred hybrid risk score generation machine learning models described and enabled by various embodiments of the present invention often require relatively little computationally resources (including processing resources and memory resources) to execute. This is because genetic programming operations (e.g., symbolic regression operations) are able to infer often algebraic relationships between inputs to the inferred hybrid risk score generation machine learning models, a feature that both reduces the runtime cost of performing predictive inferences using the noted inferred hybrid risk score generation machine learning models and improves the need for storing complex configuration data for the inferred hybrid risk score generation machine learning models in order to enable performing predictive inferences using the inferred hybrid risk score generation machine learning models. In this way, various embodiments of the present invention improve both computational efficiency and storage-wise efficiency of performing risk score generation predictive data analysis and make important technical contributions to the field of predictive data analysis in relation to machine learning techniques for generating risk scores.

FIG. 4 is a flowchart diagram of an example process 400 for generating an inferred hybrid risk score generation machine learning model. Via the various steps/operations of the process 400, the predictive data analysis computing entity 106 can generate a model that is configured to enable efficient hybrid risk score generation using a fewer number of preconfigured parameters relative to various conventional deep learning models.

The process 400 begins at step/operation 401 when the predictive data analysis computing entity 106 identifies a trained hybrid graph-based machine learning model. In some embodiments, the predictive data analysis computing entity 106 retrieves configuration data (e.g., parameter data, hyper-parameter data, and/or the like) for the trained hybrid graph-based machine learning model from the storage subsystem 108. In some embodiments, the predictive data analysis computing entity 106 performs one or more model training operations to generate configuration data (e.g., parameter data, hyper-parameter data, and/or the like) for the trained hybrid graph-based machine learning model.

The trained hybrid graph-based machine learning model is a trained machine learning model that is configured to process one or more graph-based feature embeddings for a patient data object in order to generate an inferred hybrid risk score for the patient data object. The trained hybrid graph-based machine learning model may be configured to receive, as at least a part of its inputs, one or more graph-based feature embeddings for a patient data object, where a graph-based feature embedding may be a vector of one or more values that are determined based at least in part on a risk tensor of one or more risk tensors for the patient data object. In some embodiments, the trained hybrid graph-based machine learning model may include: a plurality of graph-based machine learning models (e.g., including one or more graph convolutional neural network machine learning models), where each graph-based machine learning model is configured to process a graph-based feature embedding having a particular graph-based feature embedding type to generate a per-model machine learning output, and an ensemble machine learning model that is configured to aggregate/combine per-model machine learning outputs across various graph-based machine learning models to generate the inferred hybrid risk score for the patient data object. For example, a trained hybrid graph-based machine learning model may include: a first graph-based machine learning model that is configured to process a graph-based feature embedding determined based at least in part on genomic data (e.g., based at least in part on a genomic risk tensor) for a patient data object in order to generate a first per-model machine learning output, a second graph-based machine learning model that is configured to process a graph-based feature embedding determined based at least in part on clinical data (e.g., based at least in part on a clinical risk tensor) for a patient data object in order to generate a second per-model machine learning output, a third graph-based machine learning model that is configured to process a graph-based feature embedding determined based at least in part on behavioral data (e.g., based at least in part on a behavioral risk tensor) for a patient data object in order to generate a third per-model machine learning output, and an ensemble machine learning model that is configured to aggregate/combine the first per-model machine learning output, the second per-model machine learning output, and the third per-model machine learning output in order to generate the inferred hybrid risk score for the patient data object. In some embodiments, the trained hybrid graph-based machine learning model is trained (e.g., via one or more end-to-end training operations) using ground-truth hybrid risk scores for a set of ground-truth graph-based feature embeddings for each training patient data object of a set of training patient data objects.

In some embodiments, performing step/operation 401 includes generating the trained hybrid graph-based machine learning model, for example in accordance with the process that is depicted in FIG. 5. The process that is depicted in FIG. 5 begins at step/operation 501, when the predictive data analysis computing entity 106 performs a set of explanatory data analysis operations on patient data associated with a set of ground-truth patient data objects to generate, for each ground-truth patient data object of the set of ground-truth patient data objects, a set of ground-truth risk tensors. In some embodiments, the predictive data analysis computing entity 106 performs explanatory data analysis on relevant data sets associated with a patient data object to determine a set of data inferences, such as clinical inferences, genomic inferences, medication inferences, treatment inferences, electronic medical record (EMR) inferences, claims-related inferences, social health determinant inferences, patient-reported outcome inferences, primary care inferences, medical image inferences, and/or the like. In some embodiments, the data inferences are used to determine ground-truth risk tensors.

In general, a risk tensor may describe a tensor data object that includes a set of subject-matter-defined data items associated with a patient data object. In some embodiments, a risk tensor describes a heterogeneous group of data that are related by the underlying risk tensor. Examples of risk tensors include a genomic risk tensor that includes genomic data associated with a patient data object, a behavioral risk tensor that includes behavioral data associated with a patient data object, a clinical risk tensor that includes clinical data associated with a patient data object, a demographic risk tensor that includes demographic data associated with a patient data object, a health history risk tensor that includes health history data associated with a patient data object, and/or the like.

For example, a genomic risk tensor may describe at least one of ribonucleic acid (RNA)-seq data, complex molecular biomarkers relating to oncology (e.g. tumor mutational burden), single nucleotide polymorphisms, deoxyribonucleic acid (DNA) methylation data from panels, and/or the like. In some embodiments, all of the noted data items may be grouped, because they are all related to the genomic risk profile for a given disease, even though the data items are different, relate to different aspects of the genome, and come in different file formats (e.g. FASTQ files for DNA data, .IDAT files for Illumina Infinium HumanMethylation450 chip data, and/or the like). In some embodiments, if specific data items are assumed, from existing clinical practice, to be highly influential (e.g. smoking status and pack history for lung cancer), then a confidence score in the relevance of each risk tensor, and the necessary volumes of data, may be generated. The output from the confidence score can be used to assess whether there are sufficient data to adopt the risk tensor data, or whether additional data are recommended (e.g. data augmentation is needed in the case of medical image data). In some embodiments, when a risk tensor is used to generate a trained hybrid graph-based machine learning model (e.g., by generating ground-truth graph-based feature embeddings that are used as inputs during the training of a hybrid graph-based machine learning model), the risk tensor is referred to as a ground-truth risk tensor. In some embodiments, when a risk tensor is used to generate inferred hybrid risk scores that are in turn used to generate an inferred hybrid risk score generation machine learning model, the risk tensor is referred to as a prior risk tensor.

At step/operation 502, the predictive data analysis computing entity 106 generates, for each ground-truth patient data object of the set of ground-truth patient data objects, a set of refined ground-truth risk tensors based at least in part on the set of ground-truth risk tensors for the ground-truth patient data object. However, while various embodiments of the present invention describe refining risk ground-truth tensors to generate refined ground-truth risk tensors, a person of ordinary skill in the relevant technology will recognize that in some embodiments ground-truth risk tensors may be automatically adopted as refined risk tensors and thus refinement operations may be skipped.

In some embodiments, to perform step/operation 502, the predictive data analysis computing entity 106 generates a confidence score for the constituent data in each particular ground-truth risk tensor. The confidence score for a ground-truth risk score may be generated based at least in part on the volume of the constituent data, the estimated magnitude of the signal strength or statistical power of a given feature (e.g. Cohen's d score for effect size) of the constituent data, constituent data completeness, and quality and the presence of redundant and highly-correlated genomic variants and collinear features among the constituent data. In some embodiments, if the confidence score for a given ground-truth risk tensor fails to satisfy a confidence score threshold (e.g., falls short of the minimum threshold score for adaptation by the predictive data analysis computing entity 106 as for example determined by expert data scientists), then the failure is flagged and the predictive data analysis computing entity 106 will attempt automatically to source new data. There are several different ways that this could be performed, depending upon the specific type of the ground-truth risk tensor: for example, if the confidence score was low for a genomic risk tensor, the predictive data analysis computing entity 106 may interact with the application programming interfaces (APIs) of public-domain genomics data repositories, such as the Sequence Read Archive (available online at https://www.ncbi.nlm.nih.gov/sra), to acquire supplementary data. For a clinical risk tensor, the predictive data analysis computing entity 106 may query suitable EMR data sources for more historical data, or perform data augmentation on medical image data. This process may continue until a sufficient threshold confidence score is reached (at which point a latest state of a ground-truth risk tensor may be adopted as a refined ground-truth risk tensor), or as a last resort a notification to a human operator is transmitted after a defined number of tensor augmentation operations are performed.

At step/operation 503, the predictive data analysis computing entity 106 generates, for each ground-truth patient data object of the set of ground-truth patient data objects, a set of ground-truth graph-based feature embeddings based at least in part on the set of refined ground-truth risk scores for the ground-truth patient data object. In some embodiments, to perform step/operation 503, the predictive data analysis computing entity 106 performs at least one of the following on each set of refined ground-truth risk tensors for a ground-truth patient: one or more data quality operations, one or more data engineering operations, one or more first-order feature engineering operations, and/or the like.

A graph-based feature embedding may describe a graph-based representation of a risk tensor. In some embodiments, to generate a graph-based representation of a risk tensor, the predictive data analysis computing entity 106 may embed/convert/transform data items in the given risk tensor into a graph (e.g., a multiplex graph) representation (e.g., by converting the risk tensor into a graph embedding, for example by using a Node2Vec feature embedding routine). For example, given a genomic risk tensor, if suitable genomic networks for any diseases under consideration are available from the Kyoto Encyclopedia of Genes and Genomes (KEGG) resource (e.g. for non-small cell lung cancer the genomic pathway, available online at https://www.genome.jp/kegg-bin/show_pathway?hsa05223), then the pathway may be converted to a graph representation in order to generate a graph-based feature embedding for the genomic risk tensor. In some embodiments, when a graph-based feature embedding is used to generate a trained hybrid graph-based machine learning model (e.g., by using ground ground-truth graph-based feature embeddings as inputs during the training of a hybrid graph-based machine learning model), the graph-based feature embedding is referred to as a ground-truth graph-based feature embedding. In some embodiments, when a graph-based feature embedding is used to generate inferred hybrid risk scores that are in turn used to generate an inferred hybrid risk score generation machine learning model, the graph-based feature embedding is referred to as a prior graph-based feature embedding.

At step/operation 504, the predictive data analysis computing entity 106 generates the trained hybrid graph-based machine learning model based at least in part on the set of ground-truth graph-based feature embeddings for each ground-truth patient data object of the set of ground-truth patient data objects. In some embodiments, to perform step/operation 504, the predictive data analysis computing entity 106 trains a Graph Neural Network Deep Learning model (GNN-DL) for each ground-truth risk tensor based at least in part on the data in that particular ground-truth risk tensor (e.g., as described by the ground-truth graph-based feature embedding for the particular ground-truth risk score). In some embodiments, the specific type of deep learning models may be determined based at least in part on context and representation of the genomic information in the knowledge graph. The algorithm for performing inference in the graph may also be determined by context, such that its particular inductive bias is deemed to be a reasonable match to the data within each particular ground-truth risk tensor.

In some embodiments, to generate a graph-based machine learning model that is configured to process genomic data to generate a per-model machine learning output, depending on the types of genomic data in the genomic risk tensor and the availability of an algorithm to accommodate variants more complex than single-nucleotide polymorphisms (SNPs), the predictive data analysis computing entity 106 begins with an initial equation typical of a polygenic risk score (e.g., an equation characterized by weighted sum of risk alleles) with additional terms for other variants derived from "best guess" terms in the initial equation for the PRS for the disease(s) under consideration. For each of the remaining types of patient data, the predictive data analysis computing entity 106 may utilize a suitable existing risk model (or clinical prediction model) that is reasonably applicable to the data with that specific risk tensor and to the disease(s) in question. These may be the starting (candidate) equations for that particular GNN-DL model, and may be used to bootstrap the overall risk score for the disease under consideration. A summary of exemplary clinical prediction models may be found here: https://www.bmj.com/content/bmj/365/bmj.1737.full.pdf.

In some embodiments, as part of step/operation 504, the predictive data analysis computing entity 106 may partition the existing data to create a hold-out data set for positive cases of the disease(s) under consideration. The positive class may be associated with patient data objects that are related to the patients and that have a confirmed diagnosis for the disease(s) under consideration. The training of each model, on a specific risk tensor, may be performed in an end-to-end manner.

Returning to FIG. 4, at step/operation 402, the predictive data analysis computing entity 106 generates the inferred hybrid risk score generation machine learning model using the trained hybrid graph-based machine learning model. In some embodiments, the predictive data analysis computing entity 106 generates a model that relates a set of prior graph-based feature embeddings for a set of prior patient data objects to a set of inferred hybrid risk scores for the set of prior patient data objects as generated by the inferred hybrid risk score generation machine learning model, and then generates the inferred hybrid risk score generation machine learning model based at least in part on the noted model.

An inferred hybrid risk score generation machine learning model may be a model that relates one or more graph-based feature embeddings for a patient data object to an inferred hybrid risk score generation machine learning model. For example, the inferred hybrid risk score generation machine learning model may be determined by performing one or more genetic programming operations (e.g., including one or more symbolic regression operations) based at least in part on sets of prior graph-based feature embeddings for a set of prior patient data objects and a set of corresponding inferred hybrid risk scores for the set of prior patient data objects, where an inferred hybrid risk score for a prior patient data object may be determined by processing the set of prior graph-based feature embeddings for the prior patient data object using a trained hybrid graph-based machine learning model, and where the set of prior graph-based feature embeddings for a prior patient data object may be supplied as input variables and/or as regressor variables for the one or more genetic programming operations performed to generate the inferred hybrid risk score generation machine learning model. The inferred hybrid risk score generation machine learning model may be configured to process, as inputs, a set of graph-based feature embeddings and generate, as an output, an inferred hybrid risk score, where each graph-based feature embedding may be a vector, and where each inferred hybrid risk score may be an atomic value or a vector.

In some embodiments, step/operation 402 may be performed in accordance with the process that is depicted in FIG. 6. The process that is depicted at step/operation 601, when the predictive data analysis computing entity 106 generates an inferred hybrid risk score for each prior patient data object of a set of prior patient data objects by processing a set of prior graph-based feature embeddings for the prior patient data object using the trained hybrid graph-based machine learning model in order to generate the inferred hybrid risk score for the prior patient data object. In some embodiments, as part of step/operation 601, the predictive data analysis computing entity 106: (i) for each of the graph-based machine learning models associated with the hybrid graph-based machine learning model, partitions ground-truth graph-based feature embedding sets for validation and/or hyper-parameter tuning, and (ii) trains each of the graph-based machine learning models associated with the hybrid graph-based machine learning model using a partitioned subset of the ground-truth graph-based feature embedding sets that is reserved for training of the hybrid graph-based machine learning model.

An inferred hybrid risk score may be a risk score that is generated by a trained hybrid graph-based machine learning model by processing a set of graph-based feature embeddings for a corresponding patient data object. For example, the inferred hybrid risk score for a particular patient data object may be generated by processing (using a trained hybrid graph-based machine learning model) the genomic graph-based feature embedding for the particular patient data object as determined based at least in part on the genomic risk tensor for the particular patient data object, the clinical graph-based feature embedding for the particular patient data object as determined based at least in part on the clinical risk tensor for the particular patient data object, and the behavioral graph-based feature embedding for the particular patient data object based at least in part on the behavioral risk tensor for the particular patient data object. The inferred hybrid risk score may be a vector.

At step/operation 602, the predictive data analysis computing entity 106 determines a set of regressor variable values for each prior patient data object of a set of prior patient data objects based at least in part on the set of prior graph-based feature embeddings for the prior patient data object. In some embodiments, using the initial candidate equations for the per-model machine learning output associated with each individual graph-based feature embeddings, the predictive data analysis computing entity 106 determines the regressor variables. In some embodiments, the regressor variables are determined based at least in part on techniques for determining separate and interpretable internal functions as described in Crammer et al., "Discovering Symbolic Models from Deep Learning with Inductive Biases" (2020), arXiv:2006.11287v2, available online at https://arxiv.org/pdf/2006.11287.pdf. In some embodiments, a priori, the predictive data analysis computing entity 106 over-estimates the number of regressor variables so that the algorithm can reduce the parameter space of the inferred hybrid risk score generation machine learning model. In some embodiments, a regressor variable may be any feature, or feature-engineered, variable that is used in a predictive model as an input to the predictive model.

At step/operation 603, the predictive data analysis computing entity 106 performs a set of genetic programming operations on each prior patient data object of a set of prior patient data objects to generate the inferred hybrid risk score generation machine learning model. In some embodiments, at step/operation 603, using the initial clinical prediction models, and weighted sum of risk alleles (in the case of the genomic risk tensor) or existing outline clinical risk model for the disease(s) in question, the predictive data analysis computing entity performs symbolic regression on each graph-based feature embedding to generate the simplest and most accurate risk model for that graph-based feature embedding. In some embodiments, the genetic programming operations enable a refinement method between the individual graph-based machine learning models of the trained hybrid graph-based machine learning model. The outputs of the genetic programming operations may be in the form of a graph, where the nodes represent mathematical building blocks and edges represent parameters, coefficients and/or system variables. In some embodiments, the one or more genetic programming operations comprise one or more symbolic regression operations, such as one or more symbolic regression operations performed in accordance with the techniques disclosed in Schmidt et al., "Symbolic Regression of Implicit Equations" in *Genetic programming Theory and Practice VII* pp 73-85 (2009), available online at https://link.springer.com/chapter/10.1007/978-1-4419-1626-6_5.

In some embodiments, step/operation 603 may be performed using one or more modeling generation epochs, where performing operations corresponding to a particular model generation epoch may be performed in accordance with the process that is depicted in FIG. 7. The process that is depicted at FIG. 7 begins at step/operation 701, when the predictive data analysis computing entity 106 performs one or more per-embedding genetic programming operations with respect to each prior graph-based feature embedding for the prior patient data object to generate a per-embedding genetic programming modeling data object for the prior graph-based feature embedding. The per-embedding genetic programming modeling data object for a prior graph-based feature embedding for a patient data object may be a model that relates the prior graph-based feature embedding to an inferred hybrid risk score for the patient data object.

At step/operation 702, the predictive data analysis computing entity 106 performs a set of cross-model interactions across each per-embedding geniting programming modeling data object for a prior graph-based feature embedding to generate an overall inferred risk model for the model generation epoch. In some embodiments, at each model generation epoch, the predictive data analysis computing entity 106 performs cross-tensor interaction across the per-embedding geniting programming modeling data objects to generate an overall inferred risk model for the model generation epoch. In some embodiments, step/operation 702 may be performed to optimize the final combined risk equation for the disease(s) under consideration. In some embodiments, the output from the cross-tensor symbolic regression is a candidate equation representing the overall risk for the disease(s) under consideration.

At step/operation 703, the predictive data analysis computing entity 106 evaluates the overall inferred risk model for the model generation epoch using test data to determine a testing evaluation output for the overall inferred risk model for the model generation epoch. In some embodiments, the predictive data analysis computing entity 106 tests the overall inferred risk model using the hold-out test data. In some embodiments, the final overall risk model needs to meet a pre-determined threshold for accuracy, otherwise the predictive data analysis computing entity 106 produces a warning. In some embodiments, providing additional data, utilizing additional parameters, utilizing other embedding methods, performing feature engineering, and changing model architectures to different types of graph-based machine learning models would all be considered and the entire process re-run until the accuracy threshold is met on hold-out data reserved for testing.

At step/operation 704, the predictive data analysis computing entity 106 determines the inferred hybrid risk score generation machine learning model based at least in part on the testing evaluation output. If the testing evaluation output describes that the overall inferred risk model meets accuracy requirements, the predictive data analysis computing entity 106 may adopt that the overall inferred risk as the inferred hybrid risk score generation machine learning model. However, if the testing evaluation output describes that the overall inferred risk model fails to meet accuracy requirements, a new model generation epoch may be performed. In some embodiments, if the testing evaluation output describes that the overall inferred risk model fails to meet accuracy requirements, actionable outputs are used to refine the next pass through the data once the adjustments have been made (roughly analogous to the back-propagation step in a deep neural network, and perhaps using a lifelong machine learning approach or an incremental learning approach). The inferred hybrid risk score generation machine learning model may then be assessed for simplicity, by ensuring that repeated similar terms are necessary as the model loses accuracy when they are combined.

In some embodiments, the predictive data analysis computing entity 106 enables lifelong machine learning capability for the inferred hybrid risk, so that it will continue to be updated from "real-world" feedback of its results, e.g., if it predicted that a patient with certain clinical, genomic, behavioral characteristics would be at risk of a certain condition through its generated risk equation and the inferred hybrid risk score was incorrect, this information will be fed back in to the solution (analogously to the back-prop step in a typical deep neural network) so that it can learn from its results and improve over time. In some embodiments, once all accuracy metrics are met, the inferred hybrid risk score generation machine learning model is then ready for use in a clinical trial to determine its accuracy and efficacy in real-world clinical scenarios on diverse patient groups. If the risk equation performs sufficiently in the real-world, it is deemed ready to be accepted for general clinical use in a clinical decision support solution.

In some embodiments, once generated, the inferred hybrid risk score generation machine learning model may be used to generate a hybrid risk score for a patient data object (e.g., based at least in part on graph-based feature embeddings for the patient data object). In some embodiments, generating a hybrid risk score for a patient data object includes processing a plurality of graph feature embedding data objects for the patient data object using an inferred hybrid risk score generation machine learning model to generate the hybrid risk score, wherein: (i) the inferred hybrid risk score generation machine learning model is generated using a set of genetic programming operations, (ii) the set of genetic programming operations are performed based at least in part on a set of inferred hybrid risk scores for a set of prior patient data objects, and (iii) each inferred hybrid risk score of the set of inferred hybrid risk scores is generated by processing a plurality of prior graph feature embedding data objects for a corresponding prior patient data object of the set of patient data objects using a hybrid graph-based machine learning model.

In some embodiments, the hybrid graph-based machine learning model comprises a plurality of graph-based machine learning models and an ensemble machine learning model. In some embodiments, each graph-based machine learning model of the plurality of graph-based machine learning models is configured to process a prior graph feature embedding data object of the plurality of prior graph feature embedding data objects for a prior patient data object of the set of patient data objects to generate inferred hybrid risk score of the set of inferred hybrid risk scores for the prior patient data object. In some embodiments, the plurality of graph-based machine learning models comprise one or more graph convolutional neural network machine learning models. In some embodiments, the plurality of graph feature embedding data objects comprise a genomic graph feature embedding data object. In some embodiments, the plurality of graph feature embedding data objects comprise a behavioral graph feature embedding data object. In some embodiments, the plurality of graph feature embedding data objects comprise a clinical graph feature embedding data object. In some embodiments, the set of genetic programming operations comprise a set of symbolic regression operations.

In some embodiments, once generated, the inferred hybrid risk score may be used by the predictive data analysis computing entity 106 to perform one or more prediction-based actions. Examples of prediction-based actions include: generating user interface data for one or more prediction output user interfaces and providing the user interface data to one or more client computing entities 102, displaying one or more prediction output user interfaces to an end user, generating notification data for one or more notification user interfaces and providing the notification data to one or more client computing entities 102, presenting one or more electronically-generated notifications to an end user, and/or the like.

An operational example of a prediction output user interface 800 is depicted in FIG. 8. As depicted in FIG. 8, the prediction output user interface 800 describes the inferred risk score 801 for lung cancer for an identified patient as well as explanatory metadata 802 for the inferred risk score, where the explanatory metadata may be determined based at least in part on regressor variable values for the inferred hybrid risk score generation machine learning model in relation to the identified patient.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
   receiving, by one or more processors, a hybrid risk score from an inferred hybrid risk score generation machine learning model based on a plurality of graph feature embedding data objects for a data object, wherein the inferred hybrid risk score generation machine learning model is trained by:
   receiving, from a hybrid graph-based machine learning model, a set of inferred hybrid risk scores, wherein an inferred hybrid risk score of the set of inferred hybrid risk scores is generated based on a plurality of prior graph feature embedding data objects for a prior data object of a set of prior data objects,
   determining a plurality of regressor variable values based on the plurality of prior graph feature embedding data objects for the prior data object,
   training the inferred hybrid risk score generation machine learning model based on performing a set of genetic programming operations on the set of inferred hybrid risk scores for the set of prior data objects, wherein the plurality of regressor variable values and the set of inferred hybrid risk scores is provided as input to the set of genetic programming operations, and
   storing the inferred hybrid risk score generation machine learning model in place of the hybrid graph-based machine learning model to reduce a runtime computation cost of the hybrid risk score;
   determining, by the one or more processors, explanatory metadata based on the plurality of regressor variable values associated with the inferred hybrid risk score generation machine learning model in relation to the data object; and
   providing, by the one or more processors, the hybrid risk score and the explanatory metadata to one or more client computing entities.

2. The computer-implemented method of claim 1, wherein the hybrid graph-based machine learning model comprises a plurality of graph-based machine learning models and an ensemble machine learning model.

3. The computer-implemented method of claim 2, wherein a graph-based machine learning model of the plurality of graph-based machine learning models is configured to process a prior graph feature embedding data object of the plurality of prior graph feature embedding data objects for the prior data object of the set of prior data objects to generate the inferred hybrid risk score of the set of inferred hybrid risk scores for the prior data object.

4. The computer-implemented method of claim 2, wherein the plurality of graph-based machine learning models comprises one or more graph convolutional network machine learning models.

5. The computer-implemented method of claim 1, wherein the plurality of graph feature embedding data objects comprises a genomic graph feature embedding data object.

6. The computer-implemented method of claim 1, wherein the plurality of graph feature embedding data objects comprises a behavioral graph feature embedding data object.

7. The computer-implemented method of claim 1, wherein the plurality of graph feature embedding data objects comprises a clinical graph feature embedding data object.

8. The computer-implemented method of claim 1, wherein the set of genetic programming operations comprises a set of symbolic regression operations that infer non-complex algebraic relationships between the plurality of prior graph feature embedding data objects.

9. The computer-implemented method of claim 1, wherein a prior graph feature embedding data object of the plurality of prior graph feature embedding data objects for a prior detect object is determined based on a risk tensor of a plurality of risk tensors for the prior data object.

10. A system comprising:

one or more processors; and at least one memory storing processor-executable instructions that, when executed by any one or more of the one or more processors, causes the one or more processors to perform operations comprising:

receive a hybrid risk score from an inferred hybrid risk score generation machine learning model based on a plurality of graph feature embedding data objects for a data object, wherein the inferred hybrid risk score generation machine learning model is trained by:

receiving, from a hybrid graph-based machine learning model, a set of inferred hybrid risk scores, wherein an inferred hybrid risk score of the set of inferred hybrid risk scores is generated based on a plurality of prior graph feature embedding data objects for a prior data object of a set of prior data objects, determining a plurality of regressor variable values based on the plurality of prior graph feature embedding data objects for the prior data object, training the inferred hybrid risk score generation machine learning model based on performing a set of genetic programming operations on the set of inferred hybrid risk scores for the set of prior data objects, wherein the plurality of regressor variable values and the set of inferred hybrid risk scores is provided as input to the set of genetic programming operations, and storing the inferred hybrid risk score generation machine learning model in place of the hybrid graph-based machine learning model to reduce a runtime computation cost of the hybrid risk score;

determine explanatory metadata based on the plurality of regressor variable values associated with the inferred hybrid risk score generation machine learning model in relation to the data object; and provide the hybrid risk score and the explanatory metadata to one or more client computing entities.

11. The system of claim 10, wherein the hybrid graph-based machine learning model comprises a plurality of graph-based machine learning models and an ensemble machine learning model.

12. The system of claim 11, wherein a graph-based machine learning model of the plurality of graph-based machine learning models is configured to process a prior graph feature embedding data object of the plurality of prior graph feature embedding data objects for the prior data object of the set of prior data objects to generate the inferred hybrid risk score of the set of inferred hybrid risk scores for the prior data object.

13. The system of claim 11, wherein the plurality of graph-based machine learning models comprises one or more graph convolutional neural network machine learning models.

14. The system of claim 10, wherein the plurality of graph feature embedding data objects comprises a genomic graph feature embedding data object.

15. The system of claim 10, wherein the plurality of graph feature embedding data objects comprises a behavioral graph feature embedding data object.

16. The system of claim 10, wherein the plurality of graph feature embedding data objects comprises a clinical graph feature embedding data object.

17. The system of claim 10, wherein the set of genetic programming operations comprises a set of symbolic regression operations that infer non-complex algebraic relationships between the plurality of prior graph feature embedding data objects.

18. One or more non-transitory computer-readable storage media including instructions that, when executed by one or more processors, cause the one or more processors to:

receive a hybrid risk score from an inferred hybrid risk score generation machine learning model based on a plurality of graph feature embedding data objects for a data object, wherein the inferred hybrid risk score generation machine learning model is trained by:

receiving, from a hybrid graph-based machine learning model, a set of inferred hybrid risk scores, wherein an inferred hybrid risk score of the set of inferred hybrid risk scores is generated based on a plurality of prior graph feature embedding data objects for a prior data object of a set of prior data objects, determining a plurality of regressor variable values based on the plurality of prior graph feature embedding data objects for the prior data object, training the inferred hybrid risk score generation machine learning model based on performing a set of genetic programming operations on the set of inferred hybrid risk scores for the set of prior data objects, wherein the plurality of regressor variable values and the set of inferred hybrid risk scores is provided as input to the set of genetic programming operations, and storing the inferred hybrid risk score generation machine learning model in place of the hybrid graph-based machine learning model to reduce a runtime computation cost of the hybrid risk score;

determine explanatory metadata based on the plurality of regressor variable values associated with the inferred hybrid risk score generation machine learning model in relation to the data object; and provide the hybrid risk score and the explanatory metadata to one or more client computing entities.

19. The one or more non-transitory computer-readable storage media of claim 18, wherein the hybrid graph-based machine learning model comprises a plurality of graph-based machine learning models and an ensemble machine learning model.

20. The one or more non-transitory computer-readable storage media of claim 19, wherein a graph-based machine learning model of the plurality of graph-based machine learning models is configured to process a prior graph feature embedding data object of the plurality of prior graph feature embedding data objects for the prior data object of the set of prior data objects to generate the inferred hybrid risk score of the set of inferred hybrid risk scores for the prior data object.

* * * * *